United States Patent [19]

Zaffaroni et al.

[11] Patent Number: 4,564,364
[45] Date of Patent: Jan. 14, 1986

[54] ACTIVE AGENT DISPENSER

[75] Inventors: Alejandro Zaffaroni, Atherton; Patrick S. L. Wong, Hayward, both of Calif.

[73] Assignee: ALZA Corporation, Palo Alto, Calif.

[21] Appl. No.: 498,381

[22] Filed: May 26, 1983

[51] Int. Cl.$^4$ ............................................. A61F 15/00
[52] U.S. Cl. .................................. 604/897; 604/896; 604/304; 604/307; 604/308
[58] Field of Search ............... 604/896, 304, 307, 308, 604/897

[56] References Cited

U.S. PATENT DOCUMENTS

| | | | |
|---|---|---|---|
| 3,342,183 | 9/1967 | Edenbaum | 128/268 |
| 3,598,127 | 8/1971 | Wepsic | 128/349 |
| 3,854,480 | 12/1974 | Zaffaroni | 128/260 |
| 3,921,636 | 11/1975 | Zaffaroni | 128/260 |
| 3,923,939 | 12/1975 | Baker et al. | 264/49 |
| 3,926,188 | 12/1975 | Baker et al. | 128/260 |
| 3,948,262 | 4/1976 | Zaffaroni | 128/260 |
| 3,993,072 | 11/1976 | Zaffaroni | 128/260 |
| 4,024,871 | 5/1977 | Stephenson | 128/335.5 |
| 4,031,894 | 6/1977 | Urquhart et al. | 128/268 |
| 4,057,619 | 11/1977 | Higuchi et al. | 424/14 |
| 4,201,211 | 5/1980 | Chandrasekoran et al. | 128/268 |
| 4,286,592 | 9/1981 | Chandrasekoran | 128/260 |
| 4,292,965 | 10/1981 | Nash et al. | 128/260 |

FOREIGN PATENT DOCUMENTS

| | | |
|---|---|---|
| 728198 | 6/1977 | South Africa . |
| 80/3009 | 5/1980 | South Africa ..................... 128/260 |

OTHER PUBLICATIONS

Higuchi, J. Pharm. Sci., vol. 50, No. 10 (Oct., 1961), pp. 874–875.
Higuchi, J. Pharm. Sci., vol. 52, No. 12 (Dec., 1963), pp. 1145–1149.
Chien et al., J. Pharm. Sci., vol. 63, No. 4 (Apr., 1974), pp. 515–519.

Primary Examiner—Howard S. Williams
Attorney, Agent, or Firm—Steven F. Stone; Paul L. Sabatine; Edward L. Mandell

[57] ABSTRACT

The release pattern of a dispersion type active agent dispenser can be improved by forming the device from a depleted zone containing the agent at a concentration no greater than the saturation and a non-depleted zone containing the agent dispersed in the matrix at a uniform concentration greater than saturation. The depleted zone is disposed between the surface through which the agent is to be dispensed and at least a substantial portion of the non-depleted zone with the interface therebetween disposed at a non-uniform distance from the releasing surface. Certain embodiments are particularly useful for the transdermal administration of drugs.

24 Claims, 26 Drawing Figures

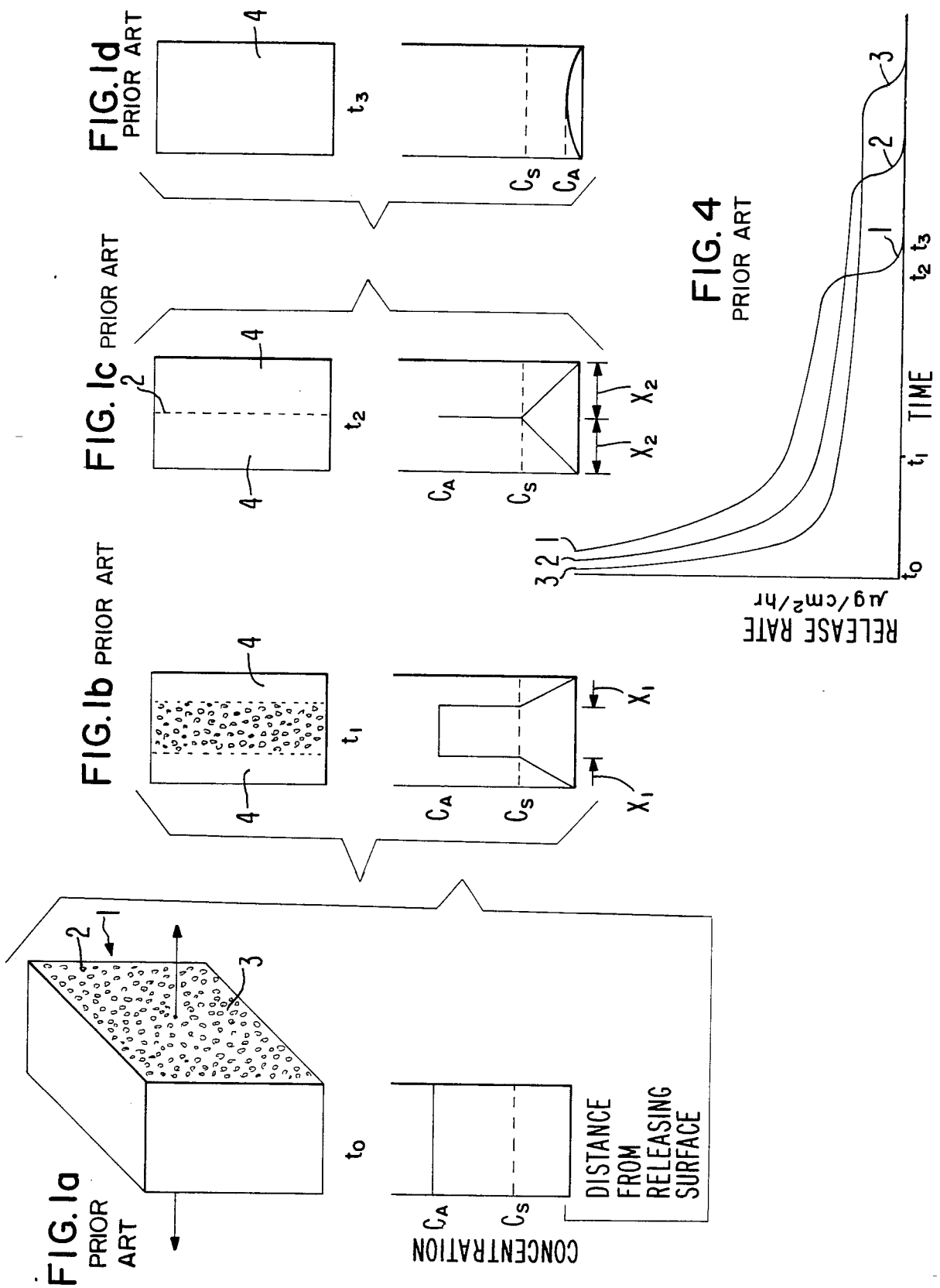

FIG. 2a PRIOR ART
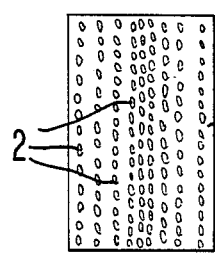
FIG. 2b PRIOR ART
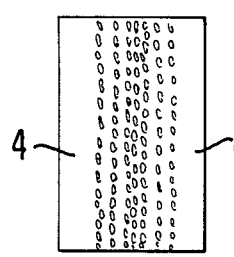
FIG. 3 PRIOR ART
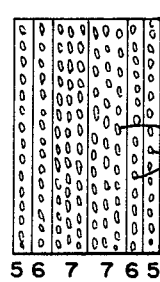
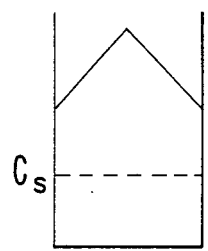
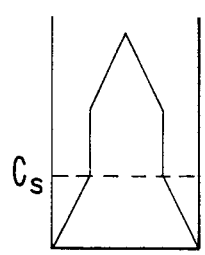
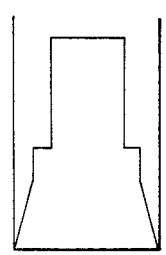
FIG. 5a
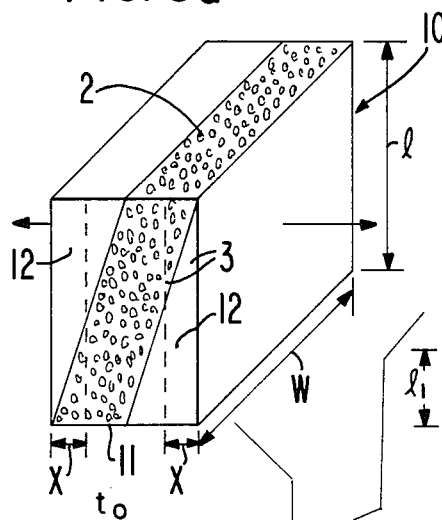
FIG. 5b
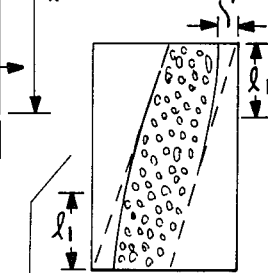
FIG. 5c
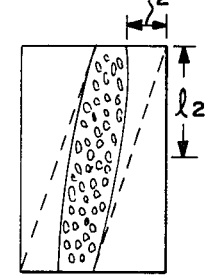
FIG. 5d
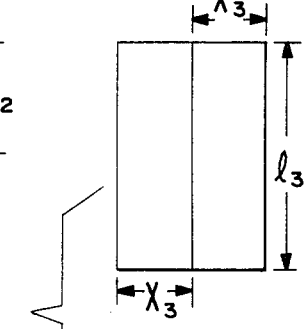
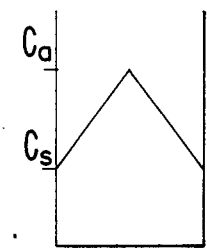
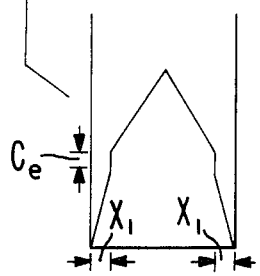
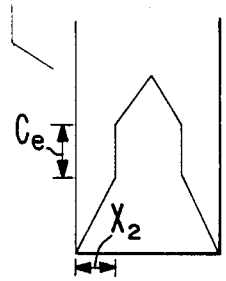
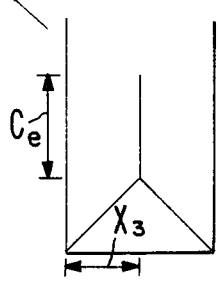

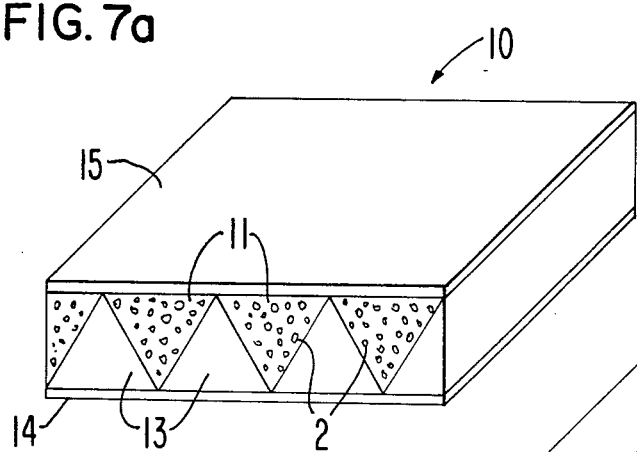
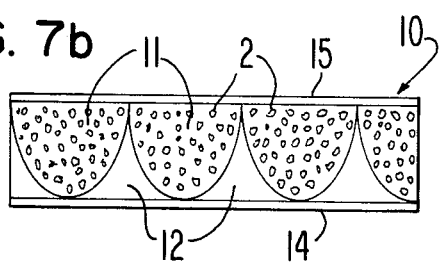
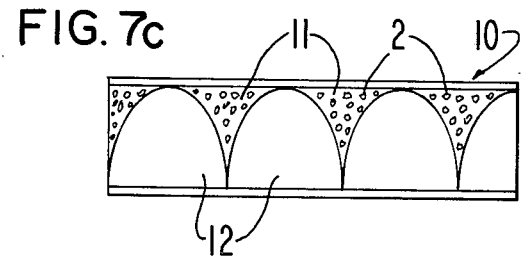
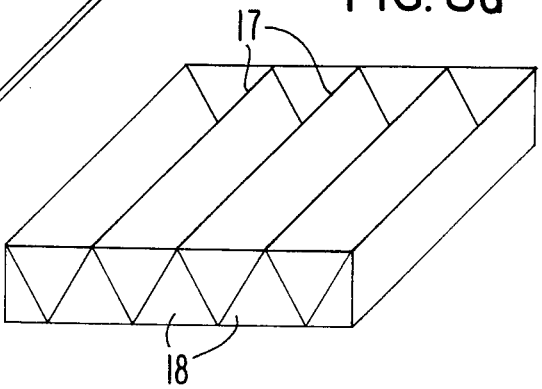
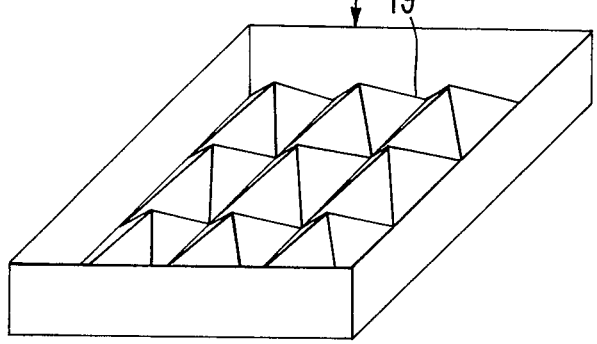
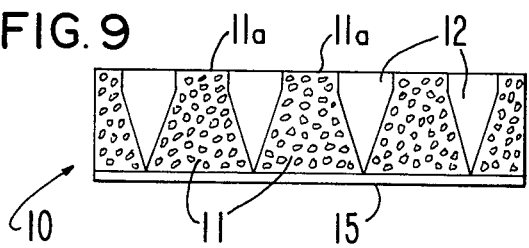
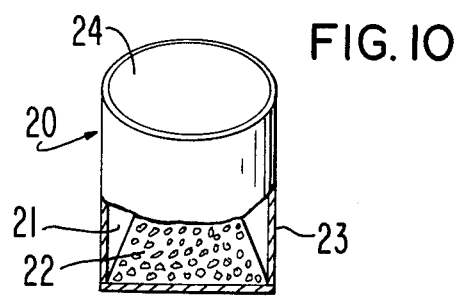
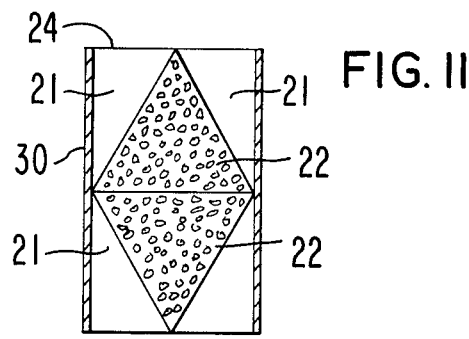

ACTIVE AGENT DISPENSER

FIELD OF THE INVENTION

This invention relates to active agent dispensers in which the agent to be dispensed is dispersed throughout a matrix and more particularly to a method and apparatus for improving the release characteristics of the agent from the dispenser.

BACKGROUND OF THE INVENTION

It is known to the art to dispense various types of biologically active agents such as drugs, hormones, nutrients, pesticides, fertilizers, bacteriocides and fungicides, for example, from a source into an environment of use. In their broadest context, these devices comprise a source or reservoir of the active agent to be dispensed which is maintained in mass transfer relationship to the environment of use. In those situations in which the rate at which the active agent is released is not particularly critical, it is possible to achieve adequate results merely by placing a mass of the material in the environment and allowing it to dissolve or diffuse or otherwise disperse into the environment. In other circumstances, however, such as where pharmaceutical products, pesticides or nutrients, for example, are involved or where it is necessary to extend delivery over a long period of time in a predictable fashion; it becomes necessary to more precisely control the release rate of the active agent from its source. When extremely precise control release of the active agent from the device is required, various structures, such as those shown in U.S. Pat. Nos. 3,854,480, 3,921,636, 3,926,188, 3,948,262, 3,993,072, 4,201,211, 4,031,894, 4,057,619, 4,286,592 and 4,292,965, all of which are incorporated herein by reference are known to the art. These devices utilize, in one form or another, release rate controlling barriers or membranes interposed between the source of the drug and the environment of use to control release rates. While such devices can be designed to produce extremely precise release rates, their structure is relatively complex, which complexity adds to the cost of the device.

At the other extreme where precise control is not required, it has been known to disperse the biologically active agent in a cream, ointment, gel or polymeric matrix which is then placed on or in the environment of use and the active agent released therefrom by diffusion. Typical systems include various medicated creams and gels used to dispense nitroglycerin, antihistamines and steroids for example, which are commercially available and such devices as shown by U.S. Pat. Nos. 4,024,871, 3,342,183, and 3,598,127.

The rate of release of a dispersed active agent at a concentration greater than saturation from such matrices has been extensively studied and analyzed. (See T. Higuchi, Rate of Release of Medicaments from Ointment Base Containing Drugs in Suspension, J. Pharm. Sci. Vol. 50, No. 10, P. 874–875 (October 1961); T. Higuchi, Mechanisms of Sustained Action Medication, J. Pharm. Sci., Vol. 52, No. 12, P. 1145–1149 (December 1963)). These papers show that the rate of active agent release from such systems normally will vary inversely with the square root of the time ($t^{-\frac{1}{2}}$) that the system is in operation. Such systems, accordingly, are characterized by an initial high release rate which then decreases relatively rapidly and continuously over the lifetime of the device. While these devices are relatively inexpensive to produce, merely requiring formation of an active agent loaded matrix, their application is limited to those situations in which this variation in release rate with time can be tolerated or in which some other element controls the rate of absorption by the body (such as the stratum corneum of the skin, for example).

Since simply dispersing an active agent through a matrix has significant cost advantages, various approaches have been proposed to improve the release characteristics of matrix systems without resorting to the use of rate controlling membranes. Geometrical approaches have been suggested, *Controlled Release of Bioactive Materials,* Edited by Richard Baker, p. 177–187, Academic Press, New York (1980) as have systems based on the relationship between solubility and diffusion coefficient, Chien et al., *Controlled Drug Release From Polymeric Delivery Devices II: Differentiation Between Partition Controlled and Matrix Controlled Drug Release Mechanisms,* J. Pharm. Sci., Vol. 63, No. 4, p. 515–519 (April 1974).

With respect to matrix systems comprising a matrix containing a suspension of a solute; the mass (M) transferred across a boundary per unit area and per unit of time (t) will be a direct function of the concentration of the solute in the matrix at saturation ($C_s$) and the diffusion coefficient ($D_s$) of the solute in the matrix and an inverse function of the distance across the boundary (h) according to Fick's law:

$$(dM/dt) = D_s C_s / h$$

As shown by Higuchi above, when an active agent is suspended in a stationary matrix at an initially uniform concentration, the agent is first released from the exposed surface causing a depletion of the suspended solute in the matrix immediately adjacent to the releasing surface. Once the concentration of the solute in this zone has been reduced to the saturation concentration, a depletion zone is formed across which a concentration gradient exists. For the ideal system with an infinite sink, the gradient ranges from zero at the releasing surface to $C_s$ at the interior boundary of the depletion zone. As agent release from the surface continues, the thickness of the depletion zone will increase. It is the distance between the surface of the matrix through which the agent is released and the interior boundary of the depletion zone which is the value of "h" in the above equation. As h increases, the time required for the agent to flow from the boundary of the depletion zone to the releasing surface increases, thereby decreasing the amount of active agent being transferred to the surface per unit of time.

In view of the above, it has also been proposed to compensate for the increase in the thickness of the depletion zone by increasing the concentration of the solute in the matrix, as the distance from the releasing surface increases. Various approaches have been suggested to accomplish this such as shown in U.S. Pat. No. 3,923,939 in which the solute is leached from a portion of the matrix adjacent to the surface; South African patent publication No. 728,198, June 15, 1977, which discloses a dispensing device comprising a core and an outer layer in which the concentration of the dispersed active agent in the core and outer layer are different (either higher or lower) and South African patent application 80/3009 filed May 20, 1980, which discloses a transdermal drug administration device comprising a polyacrylate film in which the concentration of the drug to be dispersed increases with increasing distance from the releasing surface.

While these approaches can improve the release characteristics of the device, the manufacturing techniques required to obtain the desired concentration gradient, either by forming separate compositions having different concentrations of solute dispersed in the matrix and thereafter sequentially forming the end item as in the South African patent, or by sequentially depositing additional amounts of the active agent onto a substrate as in the South African patent application or by extracting the surface of the finished device as in the U.S. and the South African patents; may closely approach the cost associated with manufacturing a rate controlling membrane system having superior properties.

According to our invention, however, we have devised a dispensing device and methods for fabricating and using the same in which a matrix composition containing a dispersion of the active agent solute at a concentration above saturation, is combined with a matrix composition containing the solute at a concentration no greater than saturation to produce an active agent dispensing device having a release rate, over a substantial portion of its life which does not vary as a function of $t^{-\frac{1}{2}}$. We are able to accomplish this desired result by designing our system such that the actual concentration of the dispersed solute in the undepleted zone of the device remains constant with time while the effective concentration of the solute increases with time, or in the alternative, varies in other predetermined patterns.

It is accordingly an object of this invention to provide a dispersion-type active agent dispenser having improved release characteristics.

It is another object of this invention to provide a monolithic active agent dispenser comprising an active agent solute suspended within a matrix at a substantially constant concentration greater than saturation and means for varying the effective concentration of said solute in a predetermined manner with time.

It is another object of this invention to provide a dispersion type active agent dispenser suitable for use in a transdermal delivery system.

It is another object of this invention to provide methods for manufacturing dispersion type active agent dispensers.

These and other objects of this invention will be readily apparent from the following description with reference to the accompanying drawings wherein:

DESCRIPTION OF THE DRAWINGS

FIG. 1(a) is a perspective view of an embodiment of the prior art and

FIGS. 1(b), (c) and (d) are sectional views of the embodiment of FIG. 1(a) at various stages of operation, each view being accompanied by a chart showing the associated concentration gradient;

FIGS. 2(a) and (b) are sectional views of another embodiment of the prior art at different stages of operation, each view being accompanied by a chart showing the associated concentration gradient;

FIG. 3 is a sectional view of another embodiment of the prior art accompanied by a chart showing the actual concentration gradient after a period of operation;

FIG. 4 is a representative plot of release rate vs. time for the embodiments of FIGS. 1–3;

FIG. 5(a) is a perspective view of an embodiment of this invention and

FIGS. 5(b), (c) and (d) are sectional views of the embodiment of FIG. 5(a) at various stages of operation, each view being accompanied by a chart of the associated average (FIG. 5a) and effective (FIG. 5b, c, and d) concentration gradient;

FIG. 7(a) is a perspective view and

FIGS. 7(b) and (c) are sectional views of other embodiments of this invention for delivering agent to the skin;

FIGS. 8(a) and (b) are perspective views of platens used to form embodiments of FIG. 7;

FIG. 9 is a sectional view through another embodiment of this invention for delivering an agent to the skin;

FIG. 10 is a perspective view, partly broken away of another embodiment of the invention;

FIG. 11 is a sectional view of another embodiment of this invention; and

DESCRIPTION OF THE INVENTION

Figure 6A:
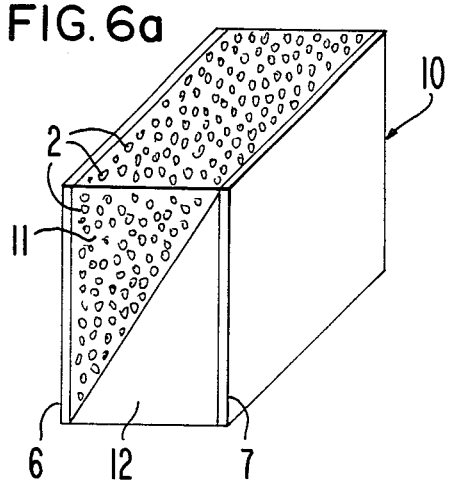
FIG. 6(a) is a perspective view.

In order to better understand the mechanism by which the desired objects of this invention are obtained, a brief discussion of the release mechanism of the prior art dispersion-type dispensing devices is useful. Referring now to FIG. 1(a), the prior art dispenser 1 shown consists of an active agent solute 2 dispersed in a matrix 3 at a uniform concentration above saturation. For the purposes of analysis, it will be assumed that the top and bottom surfaces as well as the front and back surfaces are coated or otherwise sealed with an agent-impermeable material, such that release of the active agent can only occur through the side faces shown by the arrows. In FIG. 1, FIG. 1(a) represents the device prior to, and FIGS. 1(b), 1(c) and 1(d) at varying periods of time after, immersion in an infinite sink of a solvent for the dispersed solute and the chart below each Figure shows a representative concentration gradient of the solute in the matrix at the corresponding time. In FIG. 1, the concentration gradient charts are symmetric about the center of the device since agent is being released from both side faces. It should be noted that if one side face of the device is also made impermeable similar to the front, back, top and bottom, agent release will occur only through the remaining agent permeable side; and the concentration gradient will then be asymetric as represented by one half of the chart running down the center line.

In FIG. 1 the solute 2 may be either a solid or a liquid in the form of a multiplicity of agent depots dispersed through matrix 3. The total concentration of solute is higher than the saturation concentration ($C_s$) for the agent dissolved in the matrix and at equilbrium the matrix 3 will be saturated with the solute. Thus, as shown in FIG. 1(a) the concentration gradient prior to use is substantially uniform throughout the body, the actual concentration being represented by $C_A$ which is significantly higher than $C_s$.

When the dispenser 1 is immersed in the solvent, mass transfer of the solute from the surface of the matrix to the solvent occurs. The effect of this mass transfer is to reduce the concentration of the solute in the surface zones. As the depots of the agent become depleted continued mass transfer results in a concentration gradient ranging from $C_o=0$ at the face of the dispenser, (assuming an infinite sink and ideal conditions for extraction) to $C_s$ at the inner boundary of the depleted zone. As time progresses, the solute depots inward of the releasing surface continue to be depleted such that at time, $t_1$, a depletion zone 4 will exist having a thickness $x_1$, extending inwardly from each face through which agent is being released. This depletion zone consists of the matrix 3, depleted of suspended solute, across which the concentration decreases from $C_s$ at the inner boundary to zero at the surface in contact with the solvent. This concentration gradient is shown in the chart associated with FIG. 1(b).

FIG. 1(c) represents the device at a later time, $t_2$, just prior to the moment at which all suspended solute 2 is depleted. The concentration gradient is shown in the associated chart and it can be seen that the depletion zone has increased to its maximum thickness, $X_2$, which in this case is half the total thickness of the device.

As can be seen from FIGS. 1(a)–1(c), as the agent is dispensed from the faces of the device, the thickness of the depletion zone 4 across which the concentration of the solute decreases from $C_s$ to 0 increases with time. Since, according Fick's law of diffusion, the mass flow rate varies inversely with the thickness of the diffusion barrier; the net effect is that the flow rate of the agent decreases with time. As noted above, the Higuchi analysis shows that the relationship is a function of $t^{-\frac{1}{2}}$. After all of the suspended solute is depleted as shown in FIG. 1(d), the final tail-off occurs according to a different relationship since now the thickness of the barrier is constant while the concentration gradient, $C-C_0$, representing the driving force is decreasing with time.

Curve 1—1 in FIG. 4 is representative of the release rate of an embodiment of FIG. 1, the flux corresponding to the condition of FIGS. 1(a), (b), (c) and (d) being shown at $t_0$, $t_1$, $t_2$ and $t_3$ respectively on this curve.

Referring now to FIG. 2, a similar analysis is presented for a dispenser 1 such as that described in the above identified South African Patent Application in which the concentration of the suspended solute 2 varies in a continuous manner in the matrix 3 from a first level above saturation at the surface, to a second higher level at the center. In FIG. 2, the initial condition is shown in FIG. 2(a), the concentration of the solute 2 varing uniformly from the outer surface to the center. FIG. 2(b) shows the same device at a time, $t_1$, subsequent to its immersion in an infinite sink. As can be seen a depletion zone 4 of thickness, $X_1$, has been created behind the releasing surface in a manner similar to FIG. 1. The significant difference between FIGS. 1 and 2 is that as the depletion zone 4 propagates inwardly, the concentration of the solute at the front of the depletion zone 4 increases. Since there is a continuously greater amount of suspended solute at the front, more mass must be continually transferred to reduce the concentration at the front to the saturated level. The net effect is that the rate at which the front of the depletion zone propagates inwardly continually decreases with time. Thus, the thickness of the diffusion barrier presented by depletion zone 4 will increase at a continuously decreasing rate thereby partially compensating for the increased resistance resulting from the increased thickness of the depletion zone 4. A plot of release rate vs. time of an embodiment of FIG. 2 having the same total solute loading as the device of FIG. 1, is shown as curve 2—2 in FIG. 4.

It should be noted that the device of FIG. 2 represents the limiting case of a multilayered dispenser 1 in which two or more lamina of increasing concentrations are bonded together such as shown in FIG. 3. Layers 5 contain the solute 2 dispersed in the matrix 3 at a concentration above saturation and layers 6 and 7, each contain the solute 2 at successively higher concentrations. The concentration gradient chart of FIG. 3 shows the device at a time, t, when the depletion zone has propagated halfway through layers 5. As the depletion zone migrates inwardly, in the embodiment of FIG. 3, the propagation rate will change in specific increments. Thus the rate of propagation will be highest through layers 5; at the interface between layers 5 and 6 the propagation rate will decrease to a lower rate which will remain relatively constant through layers 6 until the interface with layer 7 is reached. At that point the propagation rate will decrease to an even lower rate which will remain relatively constant until all of the dispersed solute is depleted. A plot of the release rate from the system shown in FIG. 3 can be made to closely approximate curve 2—2 in FIG. 4. As can be seen from FIG. 4, the devices of FIGS. 2 and 3 produce an improvement in the release rate over that of a simple dispersion and this improvement is obtained without the use of release rate controlling membranes. Nevertheless, the dispensers of FIGS. 2 and 3 require that the actual concentration of the suspended solute vary across the thickness of the device and this requirement increases the cost and complexity of the manufacturing process.

According to our invention, however, we are able to modify the release rate from a monolithic system from the typical $t^{-\frac{1}{2}}$ relationship to produce systems which release at a rate more constant with time, or for that matter, produce release rates which may be caused to vary in predetermined patterns with time. This result is accomplished according to our invention with a dispenser in which the actual concentration of the dispersed solute in the non-depleted zone is constant thereby eliminating the cost and complexity associated with manufacturing a device having a concentration gradient across the thickness of the non-depleted zone. We accomplish this result by providing a dispenser having, in its initial configuration, a depleted zone containing solute at a concentration no greater than saturation and a non-depleted zone containing solute at a uniform substantially constant concentration at a level above saturation. We also provide means to vary the effective concentration of the dispersed undissolved solute phase at the releasing front in a continuous, as opposed to incremental, predetermined manner with time across a substantial portion of the thickness of the dispenser. As used herein the term, "effective concentration" ($C_e$) is given by the relationships:

$$C_D = C_A - C_S \qquad (1)$$

$$C_e = (C_D A_t)/A_o \qquad (2)$$

wherein $C_A$ is the actual total concentration of the solute in the matrix in the non-depleted zone, $C_S$ is the saturation concentration of the solute in the non-depleted zone matrix material, $C_D$ is the difference in concentration of solute between the undissolved phase and the non-depleted zone, $A_o$ is the total agent releasing surface area of the dispenser, (2 lw) and A is the surface area of the non-depleted zone which is exposed to the migrating front of the depleted zone at any point in time $(2 \, l_t \, w)$.

Equation 2 above defines the dynamic conditions existing during operation of the device. The static condition prior to use can be described in a similar manner in terms of average concentration as follows:

$$\overline{C} = (C_D A_x / A_o) \quad (3)$$

wherein $\overline{C}$ is average concentration of the undissolved solute phase in the matrix material across a hypothetical surface parallel to the releasing surface and disposed at any distance, x, inwardly from the releasing surface, $C_D$ and $A_O$ are as defined above and $A_x$ is the surface area of the non-depleted zone intersecting said hypothetical surface. According to this invention means are provided by which $\overline{C}$ is caused to increase in a continuous, as opposed to incremental, predetermined pattern as the value of x increases across a substantial portion of the thickness of the dispenser.

These relationships and the means by which they are attained will be more clearly understood from the following discussion. As shown in FIG. 5(a), one embodiment of a dispensing device 10 according to this invention is shown which consists of a non-depleted zone 11 of a uniformly loaded suspension of a solute 2 dispersed in a matrix 3 at a concentration above saturation, which zone 11 is shown as having a rhomboidal cross-section, sandwiched between wedge shaped depleted zones 12 consisting of a matrix 3 having the solute therein at a concentration no greater than saturation. This forms a dispenser 10 having a rectangular cross-section adapted to release agent through the vertical faces extending perpendicular to the plane of the drawing as shown by the arrows. This may be accomplished by sealing or coating the top, bottom, front and rear surfaces as described with FIG. 1.

In a preferred embodiment of this invention, the matrix material from which the depleted and non-depleted zones are formed is the same. This produces a more homogeneous structure which is not prone to delamination at the original interface and has no clear interfacial discontinuity which could act as a barrier to mass transfer. This also results in the depleted and non-depleted zone having the same solubility and diffusivity which simplifies design and analysis of the device and its function. It should be noted, however, that the depleted zone can have a matrix material which is different from that used in the non-depleted zone, if desired.

The conditions of Equation 3 are satisified by the embodiment of FIG. 5 because the non-depleted zone intersects the releasing surfaces only at the lines forming the lower left, and the diagonally opposite, upper right corners. Thus, at the releasing surface $A_x = 0$ and according to Equation 3 $\overline{C}$ is zero. In FIG. 5a, at any distance, x, inward of the releasing surface the area $A_x$ of the non-depleted zone intersecting a plane parallel to the releasing surface is greater and will be equal to (lxw). At the center, where x is the maximum, $A_x$ equals $A_o$ and $\overline{C}$ equals $C_D$.

Various techniques can be used to fabricate a device such as shown in FIG. 5 which range from simply casting structures having the desired shape and then bonding them together prior to the time at which they have hardened to the preferred approach of coextrusion of the depleted and non-depleted zones to form the end item which would then be cut to the desired length.

An analysis of the conditions of the dispenser at various times can be made for the device of FIG. 5 in a manner similar to that for the devices of FIGS. 1–3. However, instead of actual concentrations, $C_A$, being shown on the vertical axis of the concentration gradient curves of FIG. 5b, c and d; the adjusted concentration which is the sum of the concentration of the dissolved phase and the average concentration, $\overline{C}$, as defined in Equation 3 is shown. After the device has been immersed in an infinite sink for varying periods of time, its condition will approximate that shown in FIGS. 5(b), (c) and (d), the diagonal dotted lines in these figures representing the initial orientation of the interface between the depleted and the non-depleted zones.

When the device is initially immersed in a solvent, the solute will diffuse from the solute-permeable releasing surfaces. Since the non-depleted zone 11 intersects these surfaces only at the lower left and upper right corners, it is this part of the non-depleted zone which initially becomes depleted of solute. At time $t_1$, the depleted zone will have propagated inwardly to the position shown in FIG. 5(b) causing a rounding off of the corners of the non-depleted zone 11. At $t_1$, the outer edge of the non-depleted zone 11 will be at a distance $x_1$, from the releasing surface producing an increase in the length of the interface between the depleted and non-depleted zone across which the preponderance of mass transfer from the non-depleted zone is occurring as shown by $l_1$. Although mass transfer across the interface between the depleted and non-depleted zones is complex and 3-dimensional, resulting in some loss of solute along the entire interface as shown by the difference in the dotted and solid lines in FIGS. 5(b) and (c), the preponderance (at least 90%) is being released over that area defined by $l_1 w$ wherein w is width of the dispenser 10. This value of $l_1 w$ defines the term $A_t$ in Equation 2 used to calculate $C_e$ at time $t_1$, the value of which is shown graphically as $C_e$, in FIG. 5(b).

Thus the increased resistance to the release of the solute resulting from the increase of the distance $x_1$ from the edge of the non-depleted zone 11 to the releasing surface, is compensated for by an increase in the length, $l_1$, of the interface between the depleted and non-depleted zones across which the preponderance of mass transfer occurs. Thus, although the actual concentration of the solute in the non-depleted zone is constant, the effective concentration, $C_e$, is increasing because more solute is now available for mass transfer than was available when the length of the interface was smaller. This effect continues throughout the operation of the device as can be seen from FIGS. 5(c) and (d) which represent the device at subsequent times $t_2$ and $t_3$. At $t_3$ the device is shown at the instant immediately preceding the total depletion of the non-depleted zone 11. At $t_3$, the length, $l_3$ of the boundary between the depleted and non-depleted zone is at its maximum as is the distance $x_3$ from this boundary to the surface at this time $C_{e3}$ is also at its maximum. Thus, during the operational phase of the device the relationship:

$$l_n / x_n \approx K \quad (4)$$

where K is a constant, is maintained. After $t_3$ the rate of release of the device will tail off as in the preceding embodiments.

Referring now to FIG. 6, transdermal delivery devices 10 according to this invention are shown that release from only one surface. The characteristics of these systems will approximate the characteristics exhibited by the portion of the device of FIG. 5 lying to one side of the centerline. The devices of FIG. 6 consist of a depicted zone 12 containing solute at a concentration no greater than $C_s$ and a non-depleted zone 11 having solute 2 uniformly dispersed through the matrix at a concentration greater than $C_s$. An occlusive backing 6 may be applied to the surface of the non-depleted zone opposite the releasing surface to prevent solute loss therefrom. A contact adhesive 7 preferably having negligible resistance to transfer of the solute may be applied to the agent releasing surface of the depleted zone 12 through which the solute 2 will be transferred to the skin. If an additional adhesive is used it may contain additives such as permeation enhancers, cytoprotective agents, antiseptics, anaesthetics, or a pulse dose of the agent all as is known to the art. Alternatively adhesive overlays, Velcro ® bands, elastic bands or other means can be employed to maintain solute transferring relationship to the skin if the releasing surface does not have inherent adhesive properties. The remaining sides may be sealed or otherwise coated to prevent release of solute through those surfaces if desired. Preferably device 10 will be sufficiently thin such that any release through the exposed unsealed sides would be negligible.

In FIGS. 6(a), (b), (c), (d) and (e) the orientation of the interface between the depleted zone 12 and non-depleted zone 11 is varied. The configurations of FIGS. 6(b) and (d) yield similar release patterns as do those of FIGS. 6(c) and (e).

Figure 6B:
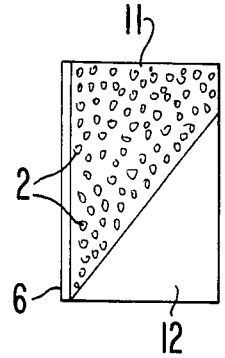
FIGS. 6(b), 6(c), 6(d) and 6(e) are sectional views of embodiments of the invention for delivering an agent to the skin.
Figure 6C:
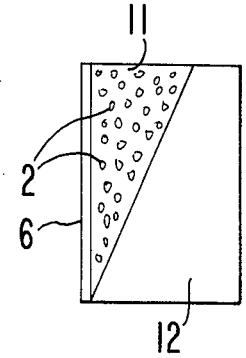
Figure 6D:
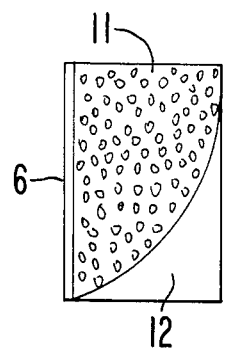
Figure 6E:
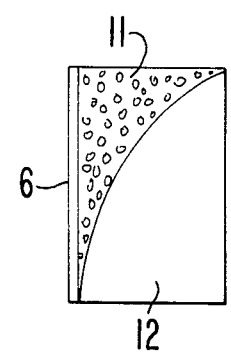

While the precise release pattern depends on many variables, in general, assuming the same total solute loading in the non-depleted zones, the embodiments of FIG. 6(b), and FIG. 6(d) will have a larger initial burst than the embodiment of FIG. 6(a) and will thereafter release at a lower rate for a longer period of time because of the lower concentration of solute in the non-depleted zone. Conversely the embodiments of FIG. 6(c) and FIG. 6(e) will have shorter initial burst than the embodiment of FIG. 6(a) but will thereafter release at a higher rate for a shorter period of time because of the higher concentrations of solute in the non-depleted zone.

Referring now to FIG. 7, other configurations of dispensers according to this invention are shown. In FIGS. 7(a), (b) and (c), dispensers 10 according to this invention for delivering an active agent to the skin, are shown consisting of an impermeable backing 15 overlaying a non-depleted zone 11 comprising an agent 2 dispersed through a matrix 3 at a concentration higher than saturation and a depleted zone 12 containing the agent to be dispensed in the matrix 3 at a concentration no greater than saturation. Preferably the matrix of depleted zone 12 is formed from the same or similar material as is the matrix of the non-depleted zone 11. If desired, a contact adhesive layer 14 can be coated on the skin proximal surface of the device although, with proper selection of the matrix material for the depleted zone 13, adequate adhesive properties to bond to the skin can be obtained. Other means for maintaining close contact with the skin in lieu of an adhesive layer can be employed such as adhesive overlays, elastic bands or Velcro ® straps, for example noted above.

In the embodiment of FIGS. 7(a), (b) and (c), the configuration of the interface between the depleted and non-depleted zone has been varied to illustrate the different release patterns that can be obtained by appropriate selection of interface configuration. If one assumes that the total solute loading in the non-depleted zones 11 of each of the embodiments of FIG. 7(a), (b) and (c) is the same; then the release patterns from these systems will bear the same general relationship to each other as observed with respect to the embodiment of FIGS 6(a), (b) and (c) respectively.

Devices of FIG. 7, can be readily formed by co-extrusion of the depleted and non-depleted zones and the deposition of the extrudate onto an impermeable backing followed by cutting of the continuously formed product into the desired size. Alternatively, casting techniques can be employed either as a continuous film casting process or a batch process. As shown in FIG. 8(a), substrate or platen 16 having the desired configuration of lands 17 and grooves 18 is shown. In FIG. 8(b) the platen is provided with a multiplicity of appropriately shaped protruberances 19, for example. The platen 16 would be treated with an appropriate release agent, as know to the art, to permit removal of the matrix, and the agent loaded dispersion cast onto the platen to the desired level. Thereafter, the backing member can be applied on the upper surface and allowed to bond thereto. The agent loaded matrix with the backing member can then be removed from the mold, inverted and used as the base onto which the depleted zone would be cast. If desired, an adhesive layer can be overcast on the depleted zone and the finished product, after setting or curing to the desired hardness, cut into desired lengths or shapes and packaged in a conventional manner. A continuous film coating process can also be employed with suitably patterned rollers replacing the platen which would emboss the desired pattern into the matrix substrate. The other zone could then be continuously film cast onto the embossed substrate.

In certain applications, where it is desired to deliver an initial dose at a relatively high rate and then a continuous dose at a lower rate the contact adhesive could be loaded with the drug as is known to the art and applied to devices having the configurations shown in FIGS. 6(a) and (b), or FIG. 7 for example. Another configuration adapted to produce a similar release pattern without a loaded adhesive layer and made by a casting or molding process is shown in FIG. 9. The dispenser 10 consists of depleted and non-depleted zones 12 and 11, respectively applied on an impermeable backing 15. The matrix material is selected to have sufficient tackiness to adhere to the skin without additional adhesive. The skin contacting portions 11a of the non-depleted zones 11 contain an amount of agent sufficient to provide the initial pulse dose. Upon depletion of the pulse the system will release at a relatively constant rate for the remainder of its functional life.

While various embodiments of this invention have been illustrated in the form of planar structures, the invention is not limited thereto. Thus, for example, FIG. 10 shows a dispenser 20 according to this invention in the form of a cylindrical plug. Dispenser 20 comprises a cylindrical plug 21 having the solute dispersed there through at a concentration no greater than saturation, which plug is formed with a conical recess into which is inserted a conical plug 22 having the solute dispersed therethrough at a uniform concentration greater than saturation. The entire dispenser 20, except for its releasing surface 24, is sealed or coated with an impermeable coating 23. The device is usable as an implant or a suppository for dispensing an agent into a body cavity or can be used for example to dispense nutrients or fertilizers into any desired environment.

A device 30 similar to that of FIG. 10, capable of releasing from two surfaces can be simply fabricated according to FIG. 11 by placing two cylindrical elements comprising depleted and non-depleted zones 21 and 22 in end to end abutment within an impermeable tube 23 such that opposite ends 24 function as releasing surfaces. In FIGS. 10 and 11 the bodies are described as having cylindrical exteriors with conical plugs. Obviously many other geometrical configurations such as rectangular prisms with tetrahedral plugs, for example, can be used.

The devices of this invention can be made from various combinations of matrix and solute materials; the specific combination of which is not an essential part of this invention. The particular combination will be selected based on criteria of solubility, permeability and chemical compatibility all as known to the art. Particularly suitable matrix materials include thermoplastic and thermosetting polymers and aqueous and non-aqueous gels. Suitable materials are known to the art and are adequately described in the above-identified patents, particularly U.S. Pat. No. 3,923,939, as are the agents to be dispensed and the environments to which they are to be dispensed. This invention is not limited to any particular combination of matrix and solute, it merely being necessary that the combination of matrix and solute be selected such that the properties of solubility, diffusivity and permeability fall within the range required to produce the desired output for a particular use from a particular sized device.

In addition to the active agent solute, per se, that is intended to be dispensed, various other materials can be mixed either with the agent or dispersed throughout the matrix. Thus permeation enhancers, anaesthetics, antiseptics, antioxidants, stabilizers, osmotic agents or other materials can be added to the primary agent to be dispensed. Combinations of two or more primary solute materials can also be dispensed simultaneously. If the dispersed solute is a material which is not readily soluble in water, it is sometimes desirable to mix within the matrix and the liquid tends to coat the interior surface of the void in which it was originally enclosed. It also prevents the formation of voids in the depleted zone, the solute dispensed being replaced by water.

Having thus generally described our invention, the following examples are representative of various specific embodiments thereof.

EXAMPLE 1

Figure 12:
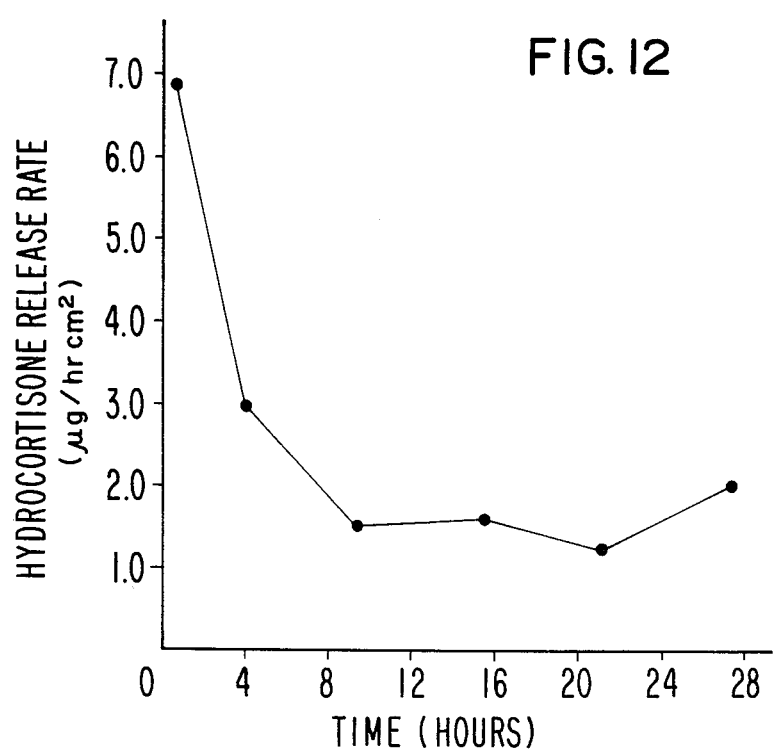
FIG. 12 is a release rate vs. time plot of the embodiment of Example 1.

Forty parts of ethylene vinyl acetate (EVA) copolymer having a 40% vinyl acetate content were blended with 60 parts of hydrocortisone alcohol on a two-roll rubber mill until a smooth dispersion was achieved. Approximately 200 milligrams of this dispersion was placed in a pre-heated mold with a one-inch circular cavity designed with a slanting plane bisecting the internal volume. The deepest portion of the mold was 0.75 millimeters. A circular, wedge shaped film having dispersed hydrocortisone alcohol at a level above saturation, was formed which film was molded at 65°0 C. for 5 minutes under 30,000 psi gauge. A similar wedge shaped film of neat EVA was placed on top of the loaded EVA wedge to form a cylinder in a cylindrical mold. The two elements were bonded at approximately 1,000 psi for one minute. The in vitro drug release profile from the neat polymer face into water at 37° C. is shown in FIG. 12.

EXAMPLE 2

A mixture of testosterone (20% w/w) with Silastic ® 382 and 0.5% Dow Corning Catalyst M is cast to a depth of 3 mm on the wedge shaped platen of FIG. 9 coated with a silicone release agent. The 3 mm depth is just above the peaks of the wedge with a peak to peak distance of 3 mm, the wedge angle is 45° to the horizontal. The mixture is cured at room temperature for 30 minutes. After curing, the drug-polymer mixture is released from the platen and placed horizontally with the wedged side face-up. Silastic ® 382+0.5% Dow Corning Catalyst M without testosterone is poured on the top of the drug mixture and cured to form a monolith having a total thickness of slightly greater than 3 mm. When placed into a releasing bath at 37° C. with the drug free Silastic face in contact with water and the drug/polymer face and sides sealed with an impermeable barrier the device will release testosterone for at least about 12 months at a rate of approximately 1.5 $\mu g/cm^2 hr$.

EXAMPLE 3

30% wt of micronized progesterone is thoroughly mixed with Dow Corning Medical Grade Silastic ® 382 containing 0.5% Dow Corning Catalyst M. The mixture is poured into a 2 cm diameter mold tilted at 5° 43' to the horizontal to the level of uppermost corner of the base and cured at room temperature for 30 minutes. The container is then placed horizontally, filled to a total depth of 2 mm with the same Silastic mixture but without the progesterone and again cured at room temperature for 30 minutes. When placed on the skin, the system will release progesterone at a rate of approximately 7 $\mu g/cm^2/hr$ for 3 weeks.

EXAMPLE 4

Fifty parts of micronized propranolol is blended with 49 parts of polyisobutylene (m.w. 400,000) and 1 part of polyethylene glycol 1000 on a two-roll rubber mill until a homogeneous dispersion is achieved. The dispersion is placed into a wedge shape mold heated to 50° C. and compressed for 5 minutes under 30,000 psi gauge. A similar wedge shaped film of neat polyisobutylene is placed on top of the loaded wedge film to form a slab of 1 mm thick. The two elements were self-bonded together for 1 minute under 1000 psi compression. The in vitro drug release from the neat polymer face into water at 37° C. is approximately 80 $\mu g/cm^2/hr$ for 2 days.

EXAMPLE 5

The progesterone loaded Silastic of Example 3 is cast into a cylindrical plug 1 cm in diameter and 4 cm long having a conical recess 1 cm in diameter at its outer end and extending into the body to a depth of 0.99 cm. This recess is filled with the drug free Silastic material of Example 3 and cured at room temperature for 30 minutes. The cylindrical plug so produced is inserted into a cup of impermeable, heat shrinkable polyethylene with its drug free surface exposed and the cup heat shrunk around the plug. The finished product is a suppository or implant capable of releasing progesterone at a rate of about 5 $\mu g/hr$ for at least a year.

Having thus generally described our invention, it is readily apparent that various modifications can be made by workers skilled in the art without departing from the scope of this invention which is limited only by the following claims wherein:

We claim:

1. A dispenser for releasing an active agent into an environment of use comprising in combination:
   (a) at least onr non-depleted zone comprising a matrix material containing said agent at a concentration greater than the saturation concentration of the agent in said matrix material; and
   (b) at least one depleted zone comprising a matrix material containing said agent at a concentration no greater than the saturation concentration of the agent in the matrix material, said depleted zone being disposed between a surface through which the agent is to be released to the environment and at least a substantial portion of said non-depleted zone with the interface between said depleted and non-depleted zones being disposed at a nonuniform distance from said releasing surface.

2. The dispenser of claim 1 wherein said interface is disposed in a plane oblique to said releasing surface.

3. The dispenser of claim 1 wherein the non-depleted zone is disposed between two depleted zones and said agent is released to the environment through two releasing surfaces.

4. The dispenser of claim 1 wherein:
   (a) said non depleted zone is in the form of a body having at least one recess extending inwardly in a convergent manner from the surface of said non depleted zone proximate the agent releasing surface of said dispenser, and
   (b) said depleted zone is disposed within said recess.

5. The dispenser of claim 4 further comprising an agent impermeable barrier disposed on the exterior of said dispenser other than the surface through which said agent is released.

6. The dispenser of claim 4 wherein said dispenser has a cylindrical exterior and said recess is conical.

7. The dispenser of claim 6 wherein said recesses comprise a plurality of grooves.

8. The dispenser of claim 6 wherein said recess comprises a plurality of indentations.

9. The dispenser of claim 4 wherein said releasing surface is the surface of said body proximate said depleted zone.

10. The dispenser of claim 4 wherein said non-depleted zone is a planar structure provided with a plurality of said recesses.

11. The dispenser of claim 1 wherein the matrix material of said depleted and non-depleted zone is the same.

12. The dispenser of claim 1 adapted to release active agent primarily through only one surface wherein said releasing surface comprises the face of said dispenser most proximate said depleted zone.

13. The dispenser of claim 12 for dispensing agent to the skin further comprising means for maintaining said releasing surface in agent transferring relationship to the skin.

14. The dispenser of claim 13 wherein said means for maintaining said releasing surface in agent trasferring relationship to the skin comprises an adhesive property of said depleted zone.

15. The dispenser of claim 13 wherein said means for maintaining said releasing surface in agent transferring relationship to the skin comprises an agent permeable conact adhesive on said releasing surface.

16. The dispenser of claim 13 further comprising an agent impermeable coating on the surface of the dispenser opposite said releasing surface.

17. The dispenser of claim 1 further comprising means for restricting said releasing surface to a predetermined portion of the exterior surface of said dispenser proximate said depleted zone.

18. The dispenser of claim 17 wherein said restricting means comprises at least in part, an agent impermeable barrier disposed on at least a portion of the exterior of said dispenser other than said releasing surface.

19. The dispenser of claim 17 wherein said restricting means comprises, at least in part, the configuration of the dispenser wherein the exposed surface area other than the releasing surface is insubstantial compared to the area of the releasing surface.

20. A dispenser for releasing an active agent into an environment of use comprising, in combination:
   (a) at least one non-depleted zone comprising a matrix material containing said agent at a substantially uniform concentration greater than the saturation concentration of said agent in said matrix material;
   (b) at least one depleted zone comprising a matrix material containing said agent at a concentration no greater than the saturation concentration of said agent in said matrix, said depleted zone being disposed between the surface through which said agent is released to the environment and at least a substantial portion of said non-depleted zone, said depleted and non-depleted zones being configured such that the average concentration of said agent in said dispenser increases with the distance from the releasing surface while the actual concentration of said agent in the non-depleted zone remains constant.

21. A method for manufacturing an active agent dispenser for releasing said agent to an environment of use through at least one releasing surface, said dispensing comprising an agent depleted zone and an agent non-depleted zone said agent depleted zone being disposed proximate said releasing surface; which method comprises:
   (a) forming a dispersion of said active agent in a matrix material at a substantially constant concentration greater than the saturation concentration of said agent in said matrix;
   (b) forming an agent depleted matrix material which contains said agent at a concentration no greater than the saturation concentration of said agent in said matrix material;
   (c) bonding said non-depleted zone to said depleted zone to form a body having said depleted zone disposed proximate said releasing surface, and
   (d) configuring said depleted and non-depleted zones such that the average concentration of said agent in said dispenser increases with the distance from the releasing surface over a substantial portion of the thickness of the dispenser.

22. The method of claim 21 further comprising the step of bonding an agent impermeable coating onto the surface of said body opposite the releasing surface.

23. The method of claim 21 wherein said body is formed by coextrusion of the depleted and non-depleted zones.

24. The method of claim 21 wherein said body is formed by casting one of said depleted and depleted zones onto the other.

* * * * *